United States Patent
Jackson (12)

(10) Patent No.: US 7,405,333 B1
(45) Date of Patent: Jul. 29, 2008

(54) PROCESS FOR THE PREPARATION OF FLUORINATED HALOCARBONS

(75) Inventor: Ronnie D. Jackson, El Dorado, AR (US)

(73) Assignee: Norphlet Chemicals, Inc., Norphlet, AR (US)

( * ) Notice: Subject to any disclaimer, the term of this patent is extended or adjusted under 35 U.S.C. 154(b) by 0 days.

(21) Appl. No.: 12/002,502

(22) Filed: Dec. 17, 2007

(51) Int. Cl.
*C07C 17/00* (2006.01)
*C07C 17/20* (2006.01)

(52) U.S. Cl. ..................... 570/165; 570/170
(58) Field of Classification Search .......... 570/165, 570/170
See application file for complete search history.

(56) References Cited

U.S. PATENT DOCUMENTS

| 4,158,675 A | 6/1979 | Potter |
| 4,967,024 A | 10/1990 | Gumprecht et al. |
| 5,185,482 A | 2/1993 | Manzer |
| 5,744,658 A * | 4/1998 | Scott et al. ............... 570/166 |

* cited by examiner

*Primary Examiner*—Jafar Parsa
(74) *Attorney, Agent, or Firm*—Richard J. Hammond

(57) ABSTRACT

A improved process is described for the preparation of a substantially pure, liquefied stream of 1,1,1,2-tetrafluoroethane by the catalyzed reaction of trichloroethylene with hydrogen fluoride to form the intermediate 2-chloro-1,1,1-trifluoroethane and then reacting said intermediate 2-chloro-1,1,1-trifluoroethane with hydrogen fluoride, in the presence of a hydrofluorination catalyst to form a reaction stream containing 1,1,1,2-tetrafluoroethane. The improvement comprises liquefying the by-product hydrogen chloride formed in the preparation of the intermediate 2-chloro-1,1,1-trifluoroethane and countercurrently passing said liquefied hydrogen chloride thru the reaction stream containing 1,1,1,2-tetrafluoroethane thereby forming a substantially pure, liquefied stream of 1,1,1,2-tetrafluoroethane and an effluent comprising gaseous hydrogen chloride.

4 Claims, No Drawings

PROCESS FOR THE PREPARATION OF FLUORINATED HALOCARBONS

FIELD OF INVENTION

The present invention relates to a process for the preparation of chlorofluoro ethanes. More particularly, an improved process for the preparation of 1,1,1,2-tetrafluoroethane is described.

DESCRIPTION OF THE RELATED ART

For decades chlorofluorocarbons have been useful chemicals for refrigeration, solvent, foam manufacture and firefighting applications. The refrigerant R-12 (difluorodichloroethane) was the standard refrigerant and found widespread use in automotive air conditioners. The discovery of the harmful nature of chlorofluorocarbons towards the Earth's protective ozone layer led to the outlawing of the manufacture and use of most of these chemicals in the 1989 Montreal Protocol. The most popular non-ozone depleting replacement for R-12 for use in automotive air conditioning units has been R-134a (1,1,1,2-tetraflororoethane).

The production of R-134a generally begins with trichloroethylene (TCE) as feedstock in a two step process. The first reaction is typically performed under catalytic conditions to produce 2-chloro-1,1,1-trifluoroethane (R-134a). This can be done in the liquid or vapor phase. In the second reaction, R-134a is further fluorinated to R-134a. See, for example, U.S. Pat. No. 5,185,482. As this second reaction is more difficult, it is most successfully performed as a high temperature vapor phase reaction over an alumina or chromia catalyst, e.g., carbon impregnated chromic oxide, chromic oxide, etc.

The first reaction can be broken down into three individual steps (see Scheme 1, Reaction 1). In a First step, a molecule of hydrogen fluoride (HF) adds across the TCE double bond to produce 1-fluoro-1,1,2-trichloroethane (R-131a). As a Second step, direct fluorine-for-chlorine exchange converts R-131a to 1,2-dichloro-1,1-difluoroethane (R-132b). Finally, in the Third step another fluorine-for-chlorine exchange occurs that converts R-132b to R-133a.

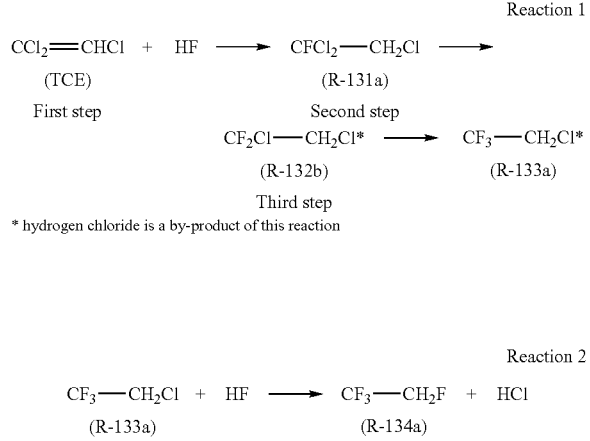

SCHEME 1

Reaction 1

$CCl_2\!=\!CHCl + HF \longrightarrow CFCl_2\!-\!CH_2Cl \longrightarrow$
(TCE)                    (R-131a)
First step          Second step
$CF_2Cl\!-\!CH_2Cl* \longrightarrow CF_3\!-\!CH_2Cl*$
(R-132b)                (R-133a)
Third step
* hydrogen chloride is a by-product of this reaction Reaction 2

$CF_3\!-\!CH_2Cl + HF \longrightarrow CF_3\!-\!CH_2F + HCl$
(R-133a)                 (R-134a)

In the subsequent reaction, R-133a is converted in the vapor phase into R-134a. See Scheme 1, Reaction 2. This reaction is well know and has been extensively studied. See, for example, U.S. Pat. Nos. 4,129,603 and 4,158,675

In the liquid phase reaction of TCE to R-133a, many transition metal halide Lewis acid catalysts have been reported to be effective. For example, the antimony (V) halides are the benchmark catalysts for fluorine-for-chlorine exchange (Swartz reaction). However they are disadvantageously reduced to Sb (III) at temperatures above 80 C. The prior art indicates that tantalum (V) halides and niobium (V) halides are the best choices for TCE to R-133a conversion. See, for example, U.S. Pat. No. 4,967,024.

In the vapor phase hydrofluorination reaction of R-133a to produce R-134a, preferred catalysts are chromium oxide or chromium oxide-containing compounds, e.g., basic chromium fluoride. These catalysts function well as temperatures above 200° C.

SUMMARY OF THE INVENTION

An improved process for the preparation of a substantially pure, liquefied stream of 1,1,1,2-tetrafluoroethane is described. In the first step, hydrogen fluoride is reacted with trichloroethylene in the presence of a hydrofluorination catalyst at a temperature below 200° C. for a time sufficient to produce a 2-chloro-1,1,1-trifluoroethane-containing reaction stream. Hydrogen chloride is obtained as a first by-product. The 2-chloro-1,1,1-trifluoroethane is then further reacted with hydrogen fluoride in the presence of a hydrofluorination catalyst at a temperature above 200° C. to form a 1,1,1,2-tetrafluoroethane-containing reaction stream. Hydrogen chloride is also obtained as a second by-product of this reaction. The first by-product hydrogen chloride is liquefied and countercurrently passed through the 1,1,1,2-tetrafluoroethane-containing reaction stream and used as a purifying refrigerant liquid in the second step of the process. A substantially pure, liquefied stream of 1,1,1,2-tetrafluoroethane and an effluent comprising purified gaseous hydrogen chloride is thereby obtained.

DETAILED DESCRIPTION OF THE INVENTION

As noted in the above description of the prior art, the process for the preparation of 1,1,1,2-tetraflororoethane (R-134a) by the catalyzed, liquid phase reaction of hydrogen fluoride with trichloroethylene (TCE) has been studied extensively. In this process, a reaction stream containing 2-chloro-1,1,1-trifluoroethane (R-133a) is produced. This reaction stream is then further reacted with hydrogen fluoride as described herein.

In addition to the reaction stream containing 2-chloro-1,1,1-trifluoroethane, an effluent of gaseous hydrogen chloride (hereinafter also referred to as the first by-product hydrogen chloride) is also produced. The stoichiometry of the reaction shows that about two moles of the gaseous hydrogen chloride are produced for each mole of starting material TCE for Reaction 1.

Typically, the amount of trichloroethylene (TCE) to hydrogen fluoride is a ratio of from about 0.1:1 to about 1.5:1 by volume. Preferably the ratio is from about 0.1:1 to 1:1 most preferably 0.25:1

The above disclosed part of the process of the present invention is carried out at a temperature of from about 100° to about 175° C., preferably 125° to about 160° C., most preferably at 140° C.

In the subsequent step of this process, the reaction stream containing 2-chloro-1,1,1-difluoroethane R-133a is converted in the vapor phase into a reaction stream comprising 1,1,1,2-tetraflororoethane R-134a. This reaction stream is a vapor and contains residual amounts of excess hydrogen fluoride and unconverted TCE, R-131a, R-132b, R-133a, as well as miscellaneous isomers of these compounds.

Reaction 1 liberates a significant amount of heat, e.g., 186.5 Btu/lb of TCE are produced from this reaction. This heat must be removed in order to condense the product 2-chloro-1,1,1-trifluoroethane (R-133a) as well as any excess of the reactant hydrofluoric acid. Additionally, it is also necessary to cool and condense the first by-product hydrogen chloride so it can be further used as provided herein.

Accordingly, it has been found to be advantageous to first liquefy the first by-product hydrogen chloride rather than immediately remove it from the process for other applications, e.g., the production of hydrochloric acid. Such liquefied hydrogen chloride is then passed countercurrently thru the gaseous reaction stream of 1,1,1,2-tetraflororoethane which contains residual amounts of TCE and R-133a, as well as miscellaneous isomers of these compounds. The countercurrent heat exchange between the liquefied hydrogen chloride and the gaseous reaction stream of 1,1,1,2-tetrafluororoethane, which contains residual amounts of TCE and R-133a as well as miscellaneous isomers of these compounds, changes the liquefied hydrogen chloride to a gas and, at this point, becomes an effluent stream. The more volatile impurities also remain in the gaseous state. However, the gaseous stream 1,1,1,2-tetrafluororoethane and heavier components condense as a liquid and are readily separated from the gaseous components of the process. The 1,1,1,2-tetrafluoroethane mixture is further purified by distillation into an R-134a product stream and an R-133a and heavier stream, see Reaction 2, which is recycled.

The liquefaction of the first by-product hydrogen chloride is typically carried out at a pressure of about 300 psig to about 30 psig and a temperature of about −61° to about 0° C. Preferably, the liquefaction is conducted at about −40° to about −5° C., most preferably—about −30° to about −20° C., with a corresponding pressure of about 250 psig to about 100 psig and about 200 psig to about 150 psig.

In particular, the liquefaction occurs by heat removal from a portion (up to about 50% of it) of the Reaction 1 liquid. This liquid typically has a temperature of from about 65° to about 150° C. It is first cooled with cooling water, followed by further cooling in an intermediate temperature chiller, thereby producing a cooled liquid having a temperature of from about −61° to about 0° C. This cooled liquid is countercurrently passed thru the remainder of the uncooled Reaction 1 liquid to condense the high boiling components such as hydrogen fluoride, 2-chloro-1,1,1-trifluoroethane and the like.

Typical prior art conventional chilling, heat removal systems accomplish the cooling by a single stage, liquid low temperature cooling at temperature of from about −10° to about −40° C. The "pumparound" heat removal process of the present invention improves the energy efficiency of the process by using two stages thereby reducing the amount of overheat chilling required by about 50% to about 75%.

A similar "pumparound" heat removal process may also be used in the Reaction 2. In that case, the reaction stream liquid is about 70° to about 80° C. and the cooled part of such liquid is from about −61° to about 0° C. Efficiencies of about 50% to about 75% are realized by using this heat removal process in Reaction 2.

The present invention is illustrated by the following examples.

EXAMPLES

Example 1

Hydrofluorination of Trichloroethylene

In a 500 milliliter Hastaloy reactor was placed 7.2 grams of $TaF_5$. The reactor was evacuated, cooled in an ice bath and 120 grams (6 mol) of anhydrous HF were added. The reactor was heated to 100° C. and 131 grams (1 mol) trichloroethylene were added all at one time. The reactor was then rapidly heated to 140° C. and maintained at this temperature for 6 hours with a pressure of 500 psi. The hydrogen chloride by-product produced as a gaseous effluent was taken off and liquefied at 300 psig and −10° C. At the conclusion of the reaction period, the contents of the reactor were vented into crushed ice. Analysis of the product obtained from the ice mixture gave a yield of 2-chloro-1,1,1-trifluoroethane of 80%. The liquefied hydrogen chloride was then utilized in the subsequent reaction.

Hydrofluorination of 2-Chloro-1,1,1-Trifluoroethane (R-133a)

Seven Hundred and twenty milligrams (0.002 mol) of tantalum pentachloride ($TaCl_5$) is charged into a 250 milliliter reactor. The reactor is evacuated and cooled with ice. Fifty grams (2.5 moles) of anhydrous hydrogen fluoride (HF) is next added to the reactor.

The resulting solution is heated with stirring to 240° C. and 13.4 grams (0.1 mol) of 2-chloro-1,1,1-trifluoro-trifluoroethane (R-133a) is added. The reactor temperature is maintained at 240° C. for 60 minutes and samples are withdrawn from the reactor headspace periodically. The reaction is monitored by GC. After about 60 minutes, the gaseous contents of the reactor are passed into the bottom of a Hastaloy tube and the liquefied hydrogen chloride obtained as by-product from the above hydrofluorination of trifluoroethylene is introduced at the top of the tube. The Hastaloy tube has a liquid collecting trap attached below the port used to introduce the gaseous contents of the reactor and a effluent vent at the top to remove effluent. Analysis of the gaseous contents of the reactor (prior to passing such contents into the Hastaloy tube and countercurrently extracting it with liquefied hydrogen chloride) show a mixture of hydrogen fluoride, 2-chloro-1,1,1-trifluoro-trifluoroethane (R-133a) and 1,1,1,2-tetrafluoroethane in a ratio of about 1:1:1. After liquefied hydrogen chloride extraction in the Hastaloy tube, a substantially pure, liquefied stream of 1,1,1,2-tetrafluoroethane is obtained.

The following table is illustrative of the temperatures required for liquefied hydrogen chloride to liquefy the gaseous 1,1,1,2-tetrafluoroethane reaction stream that is produced from the vapor phase, catalyzed reaction of hydrogen fluoride with 2-chloro-1,1,1-trifluoro-trifluoroethane. The composition of the effluent stream produced after such liquefaction is also shown. Note, that by using liquefied hydrogen chloride as a cooling means for the gaseous reaction stream produced in the 2-chloro-1,1,1-trifluoro-trifluoroethane hydrofluorination, the 1,1,1,2-tetrafluoroethane condenses while the other components of the reactions stream remain in the gaseous state. They are removed as a volatile effluent. A substantially pure liquid reaction stream of 1,1,1,2-tetrafluoroethane is obtained.

TABLE

| Pressure psig | Vapor Pressure (° C.) | | | | | | |
|---|---|---|---|---|---|---|---|
| | HCl | HF | R-133a | R-134a | R-132b | R-131a | TCE |
| 35.3 | −61 | 56.7 | 41.1 | 3.9 | 88.9 | 132.2 | 133.3 |
| 85.3 | −42 | 83.6 | 65.6 | 26.1 | 119.4 | 163.3 | 166.1 |
| 135.3 | −31 | 101.1 | 82.2 | 41.4 | 137.8 | 184.4 | 188.3 |
| 185.3 | −22 | 115.6 | 94.4 | 52.2 | 153.3 | 200.0 | 205.6 |
| 235.3 | −14 | 127.8 | 104.4 | 61.7 | 165.6 | 213.3 | 219.4 |
| 285.3 | −8 | 137.8 | 113.9 | 70.0 | 176.7 | 224.4 | N.V. |

I claim:

1. In a process for the preparation of a substantially pure, liquefied stream of 1,1,1,2-tetrafluoroethane by the steps of 1) reacting hydrogen fluoride with trichloroethylene in the presence of a hydrofluorination catalyst at a temperature below 200° C. for a time sufficient to form a 2-chloro-1,1,1-trifluoroethane-containing reaction stream and hydrogen chloride as a first by-product of said reacting and then 2) reacting the 2-chloro-1,1,1-trifluoroethane of said reaction stream with hydrogen fluoride in the presence of a hydrofluorination catalyst at a temperature above 200° C. to form a 1,1,1,2-tetrafluoroethane-containing reaction stream and hydrogen chloride as a second by-product of said reacting, the improvement comprising (a) liquefying the first by-product hydrogen chloride and then (2) countercurrently passing said liquefied hydrogen chloride through said 1,1,1,2-tetrafluoroethane-containing reaction stream thereby forming a substantially pure, liquefied stream of 1,1,1,2-tetrafluoroethane and an effluent comprising gaseous hydrogen chloride.

2. The process according to claim 1 wherein said improvement comprises carrying out said liquification of hydrogen chloride at a pressure of about 300 to about 30 psig and a temperature of about −61° to about 0° C.

3. The process according to claim 1 wherein said improvement comprises an effluent comprising a gaseous mixture of hydrogen chloride, hydrogen fluoride and 2-chloro-1,1,1-trifluoroethane.

4. The process according to claim 3 wherein said effluent is added to the reaction of step 2).

* * * * *